United States Patent
Tsinberg et al.

(10) Patent No.: US 7,217,520 B2
(45) Date of Patent: May 15, 2007

(54) MICROWELL BIOCHIP

(75) Inventors: Pavel Tsinberg, San Diego, CA (US); Pat Roycroft, Fallbrook, CA (US); Yehudit Hannah Falcovitz-Gerassi, San Diego, CA (US); Soonkap Hahn, San Clemente, CA (US)

(73) Assignee: Biocept, Inc., San Diego, CA (US)

( * ) Notice: Subject to any disclaimer, the term of this patent is extended or adjusted under 35 U.S.C. 154(b) by 275 days.

(21) Appl. No.: 10/823,021

(22) Filed: Apr. 12, 2004

(65) Prior Publication Data

US 2004/0191891 A1 Sep. 30, 2004

Related U.S. Application Data

(63) Continuation of application No. PCT/US02/32751, filed on Oct. 15, 2002.

(60) Provisional application No. 60/329,632, filed on Oct. 15, 2001.

(51) Int. Cl.
  *C12Q 1/68* (2006.01)
  *C12M 1/36* (2006.01)
  *G01N 15/06* (2006.01)
  *C07H 21/04* (2006.01)
  *C07K 5/00* (2006.01)

(52) U.S. Cl. .................. 435/6; 435/174; 435/283.1; 435/287.2; 435/288.4; 422/68.1; 536/23.1; 530/300

(58) Field of Classification Search .............. None
  See application file for complete search history.

(56) References Cited

U.S. PATENT DOCUMENTS

| | | | |
|---|---|---|---|
| 3,939,105 A * | 2/1976 | Jones et al. .............. 521/63 |
| 4,493,815 A | 1/1985 | Fernwood et al. .......... 422/101 |
| 4,526,690 A | 7/1985 | Kiovsky et al. ............ 210/335 |
| 4,734,192 A | 3/1988 | Champion et al. .......... 210/335 |
| 4,777,021 A | 10/1988 | Wertz et al. ................ 422/101 |
| 4,797,259 A | 1/1989 | Matkovich et al. ......... 422/101 |
| 4,921,809 A * | 5/1990 | Schiff et al. ................ 436/531 |
| 5,009,780 A | 4/1991 | Sarrasin ..................... 210/238 |

(Continued)

FOREIGN PATENT DOCUMENTS

EP 0339769 11/1989

(Continued)

*Primary Examiner*—BJ Forman
(74) *Attorney, Agent, or Firm*—Fitch, Even, Tabin & Flannery

(57) ABSTRACT

Microwell biochips (11) are formed from a thin flat plate (13) of polymeric material having a plurality of regularly spaced holes (15) that extend completely therethrough and create microwells. The lower end of each hole is closed by a microporous, hydrophobic, polymeric membrane (17) laminated to the undersurface of the plate which retains an aqueous test solution in the wells until a vacuum is applied to the undersurface thereof to effect draining of the solution and of any wash solution that might be subsequently added. A spot of polymerizing isocyanate-functional hydrogel is applied generally centrally to the porous membrane surface at the bottom of each well in a manner so as to cover only a minor portion of the surface and out of contact with the well sidewalls, thus leaving substantial surface area through which drainage can be readily effected. Biological capture agents are associated with the polymerizing hydrogel so as to become immobilized as a part thereof.

18 Claims, 1 Drawing Sheet

U.S. PATENT DOCUMENTS

| | | | |
|---|---|---|---|
| 5,047,215 A | 9/1991 | Manns | 422/101 |
| 5,116,496 A | 5/1992 | Scott | 210/232 |
| 5,141,719 A | 8/1992 | Fernwood et al. | |
| 5,264,184 A * | 11/1993 | Aysta et al. | 422/101 |
| 5,326,533 A | 7/1994 | Lee et al. | 422/101 |
| 5,554,536 A | 9/1996 | Rising | 435/305.1 |
| 5,667,976 A | 9/1997 | Van Ness et al. | 435/6 |
| 5,674,395 A | 10/1997 | Stankowski et al. | 210/321.75 |
| 5,679,310 A | 10/1997 | Manns | 422/102 |
| 5,843,767 A | 12/1998 | Beattie | 435/287.1 |
| 6,027,695 A | 2/2000 | Oldenburg et al. | 422/102 |
| 6,083,761 A | 7/2000 | Kedar et al. | 436/178 |
| 6,146,854 A | 11/2000 | Koster et al. | 435/91.1 |
| 6,159,368 A | 12/2000 | Moring et al. | 210/321.75 |
| 6,200,533 B1 * | 3/2001 | Blevins et al. | 422/102 |
| 6,235,520 B1 | 5/2001 | Malin et al. | 435/287.1 |
| 6,372,813 B1 * | 4/2002 | Johnson et al. | 522/114 |

FOREIGN PATENT DOCUMENTS

| | | |
|---|---|---|
| GB | 2176601 | 12/1986 |
| WO | WO 98/14277 | 4/1998 |
| WO | WO 00/50644 | 8/2000 |

* cited by examiner

MICROWELL BIOCHIP

This application is a continuation of PCT/US02/32751, filed Oct. 15, 2002 and claims priority from U.S. Provisional Application Ser. No. 60/329,632, filed Oct. 15, 2001, the disclosures of both of which are expressly incorporated herein by reference. This invention relates to devices for carrying out bioassays, to methods for making such devices, and to methods for assaying using such devices.

BACKGROUND OF INVENTION

High throughput screening is a term used to describe a method where many discrete assays are performed in parallel. Currently, the most widely established techniques utilize 96-well microtiter plates. Such microtiter plates have been used for decades in research and clinical laboratory practice, as they provide an easy method for increasing assay throughput. Typically made of polystyrene, such microtiter or microwell plates provide 6 to 96 individual wells, in which a matrix of samples can be mixed with reagents, agitated, incubated and the like, either manually or with automated handling equipment. A particular advantage of microtiter plates is that, not only can numerous samples be quickly simultaneously assayed, but alternatively, a number of different assay conditions can be employed. To obtain quantitative assay results, a beam of light is commonly scanned into each well to obtain spectroscopic information from each well.

Assays can also be performed on a surface of each individual well, such as in a sandwich immunoassay. A variety of surface-modified polystyrene microtiter plates are commercially available from different suppliers designed to fit various applications, such as ELISA or cell culture. A variety of automated equipment is also commercially available to process microtiter plates and samples.

Their ability to increase assay throughput has made microtiter plates the choice for use in many assays, e.g. those involving selective or enhanced immobilization on the surface of the wells of such plates. U.S. Pat. No. 5,741,638 describes a process of immobilizing a particular oligonucleotide sequence in a microtiter well for specific high sensitivity detection. U.S. Pat. No. 5,610,287 describes a method for non-covalently immobilizing synthetic nucleic acid molecules upon the surface of a polystyrene support, such as a microtiter plate, to allow hybridization and other nucleic acid assays to be performed in a rapid and cost-effective manner. U.S. Pat. Nos. 5,667,976, 5,712,383, and 5,747,244 describe compositions and methods for covalently immobilizing nucleic acids onto appropriate surfaces, such as wells of a microtiter plate, for similar assay purposes. U.S. Pat. No. 6,180,769 describes a method for linking negatively charged macromolecules, such as DNA and RNA, to the plastic of a microtiter plate for assay purposes.

Ways for increasing the ability to wash and to exchange fluids within a well of a microtiter plate have also been described through the use of pervious materials, e.g. a porous structure, for the bottom of a microwell plates, examples of such are shown in U.S. Pat. Nos. 4,493,815, 5,326,533, 5,679,310 and 6,146,854. The use of a vacuum manifold beneath such a microtiter plate is alleged to allow controlled and rapid evacuation of fluid from such wells. U.S. Pat. No. 5,106,496 includes a circular membrane in the bottom of each well. Millipore Corporation sells 96-well plates having a membrane bottom as their MultiScreen™ plates.

Reducing the volume of each well in a microtiter plate may allow for higher well density in a microtiter plate and thus very high throughput analysis, perhaps even approaching that of biochips. U.S. Pat. No. 6,027,695 describes a device incorporating microwells of only 5 microliters each and suggests that microtiter plates may conceivably incorporate as many as 9600 wells. Some commercial plates presently offer 1536 wells in plates where the wells have working volumes of about 1 μl–10 μl. An example of the fluid handling and control that might be used with such microwell analysis systems is described in U.S. Pat. No. 6,225,061. U.S. Pat. No. 6,235,520 describes the use of substrates with high-density microwells for measuring the response of cells in each well for drug screening, and U.S. Pat. No. 4,734,192 shows the use of a separate membrane sheet.

More recently, plates with higher densities than 96 wells per microtiter plate, e.g. 384 and greater, have begun to be commercially developed in order to provide increased throughput and reduced reagent requirements. However, such higher well densities in a conventional microtiter plate assay present three main challenges: 1) the additional cost associated with producing such high density microtiter plates, 2) the difficulties with fluid-handling due to small well volumes, and 3) difficulties with optically obtaining accurate quantitative assay results. Accordingly, the search continues for solutions to these challenges, particularly to obtaining quantitative accuracy.

SUMMARY OF THE INVENTION

The present invention provides multiwell/microwell assay plates which utilize a hydrogel polymer, preferably a polyisocyanate-functional hydrogel polymer, for immobilization of biological materials. A solid plate is formed with multiple wells wherein support material is derivatized to present biological materials that function as probes, and by localizing such onto a particular surface of each well at a predetermined location in the plate, high throughput assay capabilities are provided in a simple, versatile format. Also provided is a method for making such plates and a method for assaying using such plates.

In one more particular aspect, the invention provides a device for holding a liquid solution and allowing the reaction thereof with immobilized biological material as a part of an assay, which device comprises a plate in which there are formed a group of wells which extend completely therethrough, wherein the walls of said wells are substantially liquid impervious, a microporous material closing the bottom of each said well, and at least one spot of a polymer attached to the upper surface of said microporous bottom of each of a plurality of said wells, which spot comprises a crosslinked hydrogel polymer having biological material so immobilized on or within the polymer as to be contactable by a liquid supplied to said well.

In another more particular aspect, the invention provides a method for carrying out a biological assay, which method comprises the steps of introducing a test solution into a plurality of wells of a device in the form of a plate having a group of wells wherein a microporous material closes the bottom of each said well, and wherein at least one spot of a polymer is attached to the upper surface of said microporous bottom of each of said plurality of said wells, which spot comprises a crosslinked hydrogel polymer having biological material so immobilized on or within the polymer, after allowing opportunity for hybridization and/or binding to occur, applying a vacuum to the device to remove said solution from said wells, and optically detecting the assay results from each said well.

In yet another more particular aspect, the invention provides a method of making a device for holding immobilized biological material and exposing said immobilized biological material with a test solution as a part of an assay, which method comprises providing a plate in which there are formed a group of holes which extend completely therethrough, which holes are arranged in a regular pattern, associating a hydrophobic microporous membrane with the undersurface of said plate so as to close the bottom of each of said holes and thereby create a plurality of microwells, attaching said membrane to the undersurface of said plate in regions that surround the perimeter about each of said holes in a manner so as to create a barrier against diffusion of a liquid solution, to be supplied to said wells, through said membrane and applying at least one microdroplet of prepolymer hydrogel material to the upper surface of the membrane in each of at least a plurality of said wells in a manner so as to polymerize and cover only a minor portion of the surface area of said well bottom, whereby drainage of an aqueous solution through said hydrophobic membrane at the bottom of each said well can be effected by the application of vacuum to the undersurface of said membrane.

DETAILED DESCRIPTION OF PREFERRED EMBODIMENTS

Figure 1:
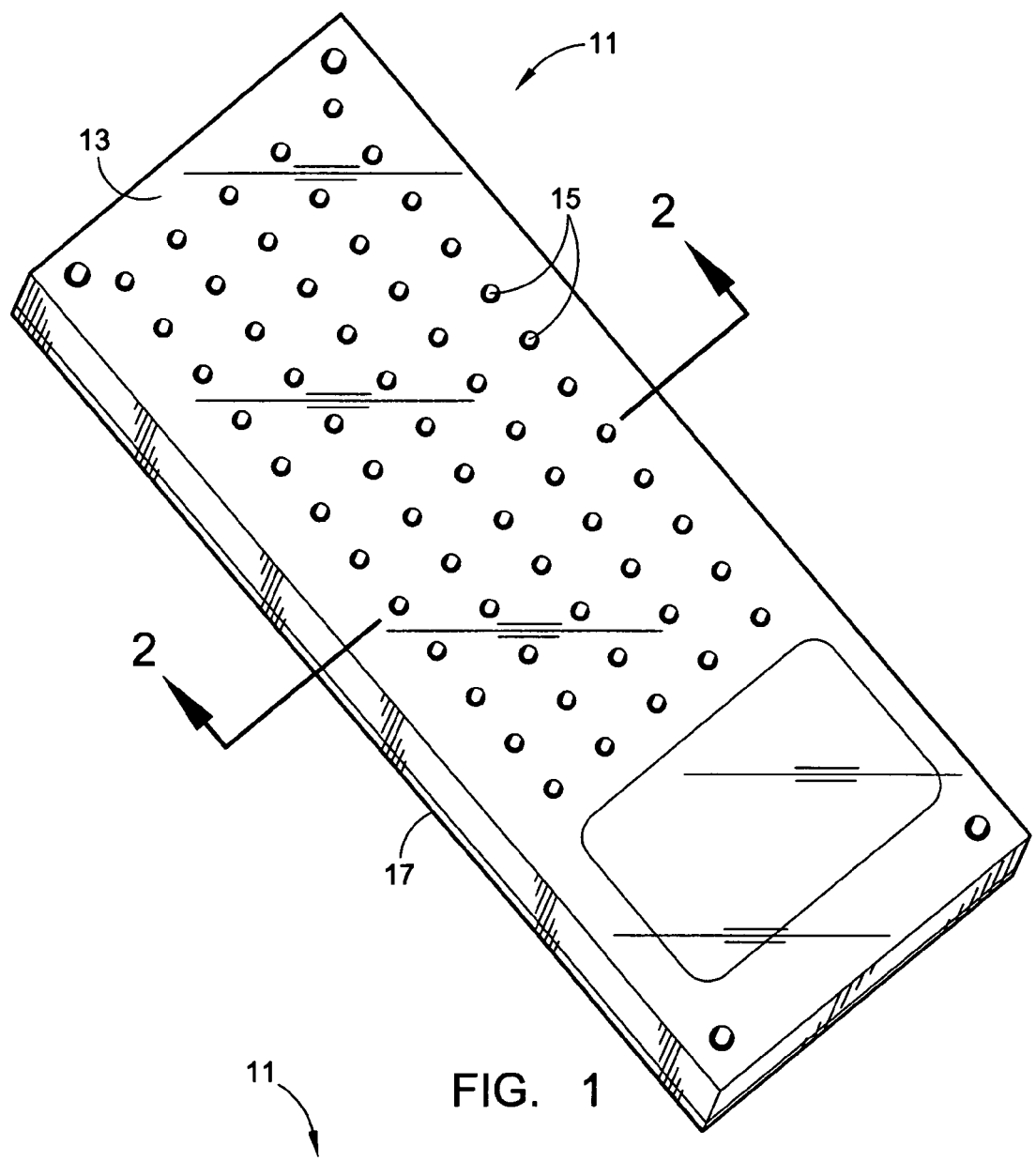
FIG. 1 is a perspective view of a microwell biochip embodying various features of the invention.
Figure 2:
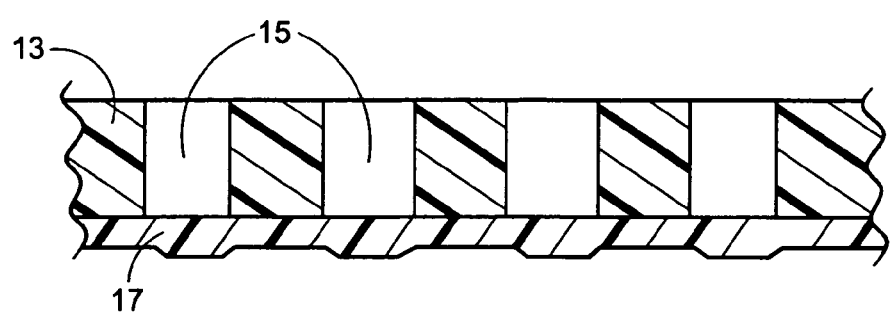
FIG. 2 is a sectional view, enlarged in size, of the biochip of FIG. 1.

The present invention comprises a solid plate in which a plurality of holes are formed and the undersurface of which is then laminated with a microporous membrane material to complete the wells. The plate is formed with, or drilled or otherwise machined to form, holes of preferably circular cross section that extend completely through its thickness before lamination with such membrane. Lamination results in a plurality of independent wells each having a continuous sidewall of the hole and a microporous membrane surface at its bottom. The resulting device is referred to as a multi-well biochip, and a sample of a prototype biochip 11 is depicted in FIG. 1.

The biochip includes a plate 13 that can be made of any suitable material commonly used in a chemical laboratory, including glass, fused silica, stainless steel and polymers, such as polyethylenes, polypropylenes, polyacrylates, polycarbonates and the like. The plate 13 may initially be a flat solid plate into which the holes 15 that extend therethrough are then formed in a regular pattern, as by drilling or chemical dissolution or any other suitable method of machining; however, plates with a desired hole pattern are preferably molded, e.g. by injection-molding, using a suitable polymer, such as polycarbonate. The thickness of such a plate usually will not exceed about 2 mm.

The holes 15, of preferably circular cross-section, may be cylindrical in shape or may be frustoconical and provide wells (when their bottoms have been closed) for assaying. The diameter of the holes 15 will be determined as a result of the size of the wells desired and the available surface area of the plate itself. The capacity of each well is a measure of the height of the well (i.e. the thickness of the plate) and the effective diameter of each well. For example, if a microwell biochip having 384 wells is desired in a plate about 1 mm thick that has the size of a standard laboratory glass slide, i.e., 1 in.×3 in. (2.54 cm×7.62 cm), the diameter of each hole may be about 1.3 mm, which will provide a maximum (or loading) volume of about 1 µl for each well, and thus an effective working volume of about 0.5 µl. A working volume of this size allows an investigator to obtain reliable results from assaying. When 384 wells are used, a standard pattern may employ 16 rows of 24 wells each.

Although a plate can be easily machined to provide such a regular hole pattern, it is considered preferable and more economical to simply form such plates by injection-molding or by some other comparable molding process for fabricating solid substrates from polymeric materials, such as rigid thermoplastic materials. Although the color of the plates may vary within a reasonable latitude, it has been found that, when optical detection systems are to be employed to determine whether a desired target has been located by an assay, it may be preferable to have the plate, and accordingly the surrounding well surface, formed from a material of dark color, preferably a black or dark grey material. To further reduce potential interference from the well itself, the plate may even more preferably have a black matte appearance. For example, black polycarbonate, black polyethylene and black Delrin™ plastic may be preferred, particularly when fluorescent assays are to be used. Other examples of acceptable plate materials include grey and clear polycarbonate and polymers referred to in the trade as 3-D lithography material. In order to decrease background "noise" during optical scanning, a plate of any color might be painted, as by spraying, to give it a matte black finish prior to its lamination to a microporous membrane as explained hereinafter; however, plates are preferably originally formed as by molding from an appropriate polymer to have such a desired finish.

On the assumption that the test solutions will normally be aqueous solutions, a microporous membrane 17 is used to close the bottom of the wells which is preferably made of a hydrophobic material, such as polyethylene, polypropylene, polytetrafluoroethylene(PTFE), polyester, polyethersulfone or the like. The hydrophobic nature of the membrane 17 assures that the solution deposited in the well will remain in the well for sufficient time for an incubation and/or hybridization reaction to occur and will not spread laterally from well to well. Once such time has passed, the application of a vacuum to the undersurface of the plate effectively drains the aqueous solution through the hydrophobic microporous membrane 17.

Lamination or attachment of the membrane 17 to the undersurface of the plate 11 may be effected in any suitable manner, as for example by adhesive or by heat sealing, e.g. ultrasonic welding. Preferably, the membrane 17 will be laminated to the undersurface of the plate by fusion thereto, most preferably through ultrasonic welding. Using such a technique, pressure is maintained between the membrane 17 and the undersurface of the perforated plate 11 while ultrasonic energy is uniformly applied thereacross. As a result, the polymeric membrane 17 fuses to the solid undersurface of the plate in the regions surrounding each hole 13, which is thus converted into a well by the microporous hydrophobic bottom surface provided by the membrane; in the region aligned with each of the holes, the membrane remains unaffected by the ultrasonic energy because of the absence of adjacent solid plate material. Because of the hydrophobic nature of the membrane, any wicking in the plane of the membrane itself below adjacent wells would be minimal;

futhermore the fusion bonding creates a positive barrier to any such wicking or diffusion laterally within the membrane itself.

To facilitate the ultimate passage of the applied aqueous solution through the porous membrane that forms the bottom of the wells, a small amount of a wetting agent or surfactant is preferably included in the solution being analyzed. When a vacuum is applied to the undersurface of the membrane, the presence of such a surfactant facilitates flow through the microporous hydrophobic polymeric membrane, which may nominally have pores in the range of about 0.3 to 1.0 µm. Pores of an average size of about 0.5 to 1 µm are considered small enough to keep aqueous solutions from diffusing in the absence of vacuum, yet they are significantly larger than the expected target molecules so as to avoid unbound target molecules getting trapped on or within the membrane.

Once the membrane has been laminated to the undersurface of the hole-containing plate, each well is then ready to be "printed" with at least one particular probe of interest using a suitable microspotting apparatus. For example, if a flat plate 1 mm thick and about 2.5 cm times about 7.5 cm is provided with a regular pattern of 384 wells of about 1.3 mm diameter, a robotic dispenser or microspotter (as known in this art) can be employed to apply a microdroplet or spot of a polymerizing hydrogel material in approximately the center of the porous bottom surface of each well. As previously mentioned, the microporous membrane 17 that is ultrasonically fused to the undersurface of the plate may be a polypropylene or PTFE membrane having pores between about 0.3 to about 1 µm, and printing may be carried out for a sample run using solid pins about 200 µm diameter. Generally, solid pins in the range of 200–700 µm as well as hollow glass pins with a similar inside diameter range are considered to be suitable. Such a pin would be first dipped in a mixture of a particular polymer, for example, an isocyanate-functional PEG-based prepolymer, so that a droplet of the mixture would adhere to the tip of such a solid pin. Because the size of the pin is substantially smaller than the diameter of the well, the pin fits easily into the center region of the well and leaves a centrally located spot of the hydrogel material on the upper surface of the membrane, which spot is out of contact with the sidewall of the well. Such spots can also be deposited using non-contact printing methods, such as ink-jet and piezo-electric deposition.

The preferred hydrogel is a PEG or PPG prepolymer that is capped with reactive isocyanates. Such prepolymers are sold under the trade name HYPOL, and such use to bind capture agents that serve as probes is described for example in U.S. Pat. No. 6,174,683 and in related International Application WO 00/65097, the disclosures of which are incorporated herein by reference. Any biological material that would be suitable for use as a probe might be used. For example, the biological material might be DNA, RNA, protein, e.g. antibodies and hormones, or even living cells. Nonpeptidic molecules useful as drugs or pharmaceuticals, e.g. small chemical compounds such as steroids, steroidal hormones, vitamins, analgesics, etc., may also be used as probes.

The hydrophobic nature of the membrane 17 deters the hydrogel from spreading so that it retains a substantially hemispherical shape and is sized to cover only a portion, e.g. less than 50%, of the surface of the bottom of well, leaving ample surface area through which draining of the aqueous solution can ultimately be carried out after such has been supplied to a well for an assay. The application of a vacuum to the undersurface of the membrane, following the passage of time during which binding/hybridization has had the opportunity to occur (which occurs when the desired target is present), promotes easy drainage of the solution. Such drainage is facilitated by including a minor amount of surfactant in the solution being assayed, or by adding such following the binding/hybridization period.

Very generally, a microwell biochip 11 with the foregoing characteristic has several advantages when compared to a standard microtiter plate system. The porous bottom arrangement, in combination with the strategic placement of hydrogel on a defined portion of the membrane bottom, reduces volume requirements for the reagent solutions, e.g. about 0.5–1 µl instead of about 1–10 µl for the more standard format generally employed in microtiter plates having either 384 wells or 1536 wells, while still permitting reliable, quantitative results to be achieved. It also affords generally easy and simple liquid transfer, and the results are readily optically readable, as by a standard fluorescence biochip scanner. The excellent binding and stability of the three-dimensional hydrogel allows a large number of probes to be immobilized in each well, thereby reducing the well surface area requirement necessary to effect the desired level of probe binding. Moreover, the device is of a straightforward, easily manufactured design affording a lower production cost, and its small size allows it to be easily stored and transported. The prototype illustrated hereinafter is compatible for use with standard slide-handling equipment, while still also being compatible with present-day dispensing and handling equipment that has been developed for use with microtiter plates.

The following examples describe a preferred embodiment of a sample microwell biochip device embodying various features of the invention and its use in assaying. Although this description sets forth the best mode presently contemplated by the inventors for carrying out their invention, it should be understood that it does not constitute limitations upon the scope of the invention which is of course defined by the claims appended hereto.

EXAMPLE 1

Preparation of Microwell Biochips

A sample microwell biochip 11 was advantageously designed to be similar in size and shape to a common (2.54×7.62 cm) microscope slide. Sixty 1.3 mm diameter holes 15 were drilled through a black polycarbonate plate 13 about 1 mm thick using a standard microtiter plate configuration (e.g. 4.5 mm pitch). In order to further decrease background during optical scanning, the plate was spray painted (prior to lamination) to give it a matte black finish.

A 0.45 µm pore size polypropylene membrane 17 (Osmonics, Inc., Minnetonka, Minn.) was laminated to the undersurface of the plate by applying spray-on adhesive to the plate and pressing the membrane in place to create this sample multiwell chip; however, it should be understood that ultrasonic welding is preferred. The membrane 17 exhibited a smooth hydrophobic surface, thus ensuring good spot morphology. This small pore membrane retains aqueous samples in the wells during binding/hybridization even when they may contain small amounts of surfactants, e.g. 1% Triton X-100, and yet it allows ready drainage through the membrane when vacuum is applied and does not entrap unbound molecules. The hydrogel cells in the wells are not physically disrupted by the use of vacuum, e.g. a pressure of about 20 in of Hg (~0.6 bar), nor as a result of the subsequent washing of the wells.

EXAMPLE 2

Printing and Hybridizing with a Microwell Protein Biochip

Protein Formulations for Printing

A mixture of Anti-transferrin antibody in Hypol (Hampshire Chemical Corporation, Lexington, Mass.) and nonspecific IgG in Hypol (as blank control) were printed and then tested with Cy3-labeled transferrin. HYPOL is an isocyanate-capped PEG prepolymer that is believed to be well-suited for this application. Both samples were formed as 3.3 weight % solutions of HYPOL (1:3:3=Prepolymer:Acetonitrile:NMP), which contained 5% Trehalose (protein preservative sugar), 100 mg/ml IgG (protein filler), 0.5% Glycerol (humectant), and either 0.8 mg/ml anti-transferrin (positive) or 1 mg/ml Bovine IgG (negative).

Printing

Printing was performed using a Cartesian array printing system (Cartesian Technologies, Inc., Irvine, Calif.) and 300 micron inside diameter glass capillary pins (Humagen Fertility Diagnostics, Inc., Charlottesville, Va.). Hydrogel spots having an approximately 310 micron diameter were printed. Three pins were used to print with anti-transferrin, and 1 pin was used to print with a blank. Each pin made 10 spots or hydrogel cells (one spot per well). After printing, the chip was cured in a humidity and temperature-controlled curing chamber for two hours at about 90% RH and about 20° C.

Hybridization and Washing

All wells containing a printed spot were filled with 1.5 μl of Cy3-labeled transferrin, and for 2 hours, the biochips were kept in a closed box with deionized water on the bottom of the box to keep its humidity high. No wetting through the membrane was observed in any of the wells. The biochip was then placed on a vacuum station which would reduce the pressure at the undersurface of the biochip to about 20 in of Hg, and the biochip was washed with a solution of 10% Triton in PBS. In most wells, the washing solution was pulled through in less than 5 minutes.

EXAMPLE 3

Imaging

In order to measure the fluorescence of microwell biochip, a charge-coupled device-based scanner was constructed using a CCD camera. Even though current dimensions of the chip allow for scans in a conventional microarray laser scanner, a CCD camera offers greater flexibility in terms of depth of focus, thickness and width of the chip. In the embodiment employed, the chip was placed on a movable stage with the CCD camera positioned directly above. Excitation light, provided by a halogen bulb, passes through a dichroic mirror, and the emission light is collected by the CCD. The dichroic mirror is set to collect data in the Cy3 fluorescent dye range. A variety of other dichroics can be substituted into the camera, thus allowing a choice from a wide range of dyes, e.g. fluorescein, Cy5. The stage can be moved either manually or through programming of different scan coordinates into the camera software. Focus, camera sensitivity, and camera exposure times are varied as necessary. By appropriately positioning the camera and the stage to be orthogonal to each other, it is possible to scan directly into the wells of the microwell biochip 11 without walls of the well interfering with the light path.

EXAMPLE 4

Laser Scanning of Microwell Biochip with Transferrin Antibody Assay

The biochip of Example 2 was also scanned with a laser scanner such as that sold as ScanArray Lite™ by Packard Biochip Technologies (Perkin Elmer). It also picked up a signal, at high laser power, for each of the wells printed with anti-transferrin, and none for the blank wells.

In summary, the novel design of this device, through miniturization, provides a device of the size of a microchip that is capable of carrying out assays comparable to those presently formed in microtiter plates. More particularly, as opposed to the need to expose substantially all of the spots in an array on a microchip to the same test solution, different test solutions can be applied to individual wells or to different groups of wells allowing great flexibility in use. Such miniturization is made possible by the unique combination of the presence of a hydrophobic microporous membrane at the bottom of a microwell and a particular hydrogel polymer that can be precisely located in a desired position thereon which is capable of immobilizing biological capture agents to serve as probes. As a result, only small volumes of an aqueous test solution need be used to carry out an assay in each individual well, whereas drainage, washing and imaging can be carried out for the entire array as a unit.

Although the invention has been described with regard to certain preferred embodiments which constitute the best mode presently known to the inventors for carrying out their invention, it should be understood that various changes and modifications as would be obvious to one having the ordinary skill in this art may be made without departing from the scope of invention which is set forth in the claims that are appended hereto. For example, within reason, any desired number of wells can be incorporated into such a multiwell biochip, and the number will normally be merely dictated by available automated equipment and standardization in the industry. In most instances a single spot of hydrogel will be positioned on the microporous membrane in each well; however, for a multiplexed environment such as that described in U.S. Pat. No. 6,083,763, multiple spots may be used so long as a substantial area remains in each well through which drainage may be effected. Various types of prepolymer hydrogel formulations can be used as disclosed in the references hereinbefore mentioned. Although optical imaging detection is preferred using a fluorescent reporter system or the like, it should be understood that other reporter systems, even radioactive reporters, may alternatively be employed. The disclosures of all the U.S. patents set forth hereinbefore are expressly incorporated herein by reference.

Particular features of the claims are emphasized in the claims which follow.

The invention claimed is:

1. A device for holding a liquid solution and allowing the reaction thereof with immobilized biological material as a part of an assay, which device comprises:

a plate in which there are formed a group of wells which extend completely therethrough, wherein the walls of said wells are substantially liquid impervious, a microporous material closing the bottom of each said well, and at least one spot of a polymer attached to the upper surface of said microporous material at the bottom of each of a plurality of said wells, which spot comprises a crosslinked hydrogel polymer having biological material so immobilized on or within the polymer as to be contactable by a liquid supplied to said well and which spot covers only a portion of the bottom surface of each well, leaving a substantial portion through which drainage can be effected.

2. The device of claim 1 wherein said polymer spots are three-dimensional and are generally centrally located on said upper surface of said microporous material.

3. The device of claim 2 wherein said biological material which is immobilized on or within said three-dimensional spots comprises DNA, RNA, protein or living cells.

4. The device of claim 1 wherein said group of wells is arranged to form a regular array.

5. The device of claim 4 wherein at least some of said plurality of wells contain different biological materials.

6. The device of claim 1 wherein the polymer is formed from an isocyanate-functional prepolymer, which prepolymer comprises polyethylene glycol or polypropylene glycol.

7. The device of claim 1 wherein said microporous material is hydrophobic and said microporosity is such that an aqueous solution supplied to said well remains therein until the application of a vacuum to the undersurface of said microporous material.

8. The device of claim 7 wherein said microporous material has an average pore size not greater than about 1 µm.

9. The device of claim 1 wherein the plate is formed of polycarbonate, polystyrene, polypropylene, polytetrafluoroethylene, polyethylene or a combination thereof and has a uniform thickness not greater than about 2 mm.

10. The device of claim 9 wherein said microporous material comprises a polymeric membrane formed of polypropylene, polytetrafluoroethylene or polyethersulfone having an average pore size of about 1 µm or less.

11. The device of claim 1 wherein said microporous material is fused to the undersurface of said plate by ultrasonic welding to densify and render such material impermeable throughout except for those regions aligned with said wells.

12. A method for carrying out a biological assay using the device of claim 1, which method comprises the steps of:
 a) introducing a test solution into wells of a device according to claim 1,
 b) after allowing opportunity for hybridization and/or binding to occur, applying a vacuum to the device to remove said solution from said wells,
 c) applying an optically active reagent to each said well, and
 d) optically detecting the assay results from each said well.

13. The method of claim 12 wherein an aqueous test solution is supplied to each of said wells and allowed to remain therein for a sufficient period for hybridization or binding to take place and wherein in each of said wells is then washed to remove unbound test solution.

14. A method of making a device according to claim 1 for holding immobilized biological material and exposing said immobilized biological material to a test solution for potential reaction therewith as a part of an assay, which method comprises:

providing a flat plate in which there are formed a group of holes which extend completely therethrough, which holes are arranged in a regular pattern, associating a hydrophobic microporous membrane with the undersurface of said plate so as to close the bottom of each of said holes and thereby create a plurality of microwells which are defined by the thickness of the plate, attaching said membrane to the undersurface of said plate in regions that surround the perimeter about each of said holes in a manner so as to create a barrier against diffusion of a liquid solution, to be supplied to said wells, through said membrane and applying at least one micro droplet of prepolymer hydrogel material to the upper surface of the membrane in each of at least a plurality of said wells in a manner so as to polymerize and cover only a minor portion of the surface area of said well bottom and associating said biological material with the polymerizing microdroplet so as to become immobilized as a part thereof, whereby drainage of an aqueous solution through said hydrophobic membrane at the bottom of each said well can be effected by the application of vacuum to the undersurface of said membrane.

15. The method of claim 14 wherein said spots are located generally centrally of the bottom surface of each well.

16. The method of claim 14 wherein said attaching is carried out by fusing a polymeric membrane to said plate by ultrasonically welding said membrane to the undersurface of said plate in regions surrounding each of said holes.

17. The method according to claim 14 wherein said spots which are applied are three-dimensional and cover less than 50% of the surface area of the bottom of each well and comprise a mixture of an isocyanate-functional hydrogel and a biological material linked thereto in a manner so as to be exposed to a liquid solution supplied to said well.

18. A multiwell device for holding liquid solutions in the wells and allowing reaction to occur between the solution and immobilized biological material in the wells as a part of an assay, which device comprises:
 a flat plate in which there are formed a plurality of wells by holes which extend completely through the thickness of said plate, wherein the sidewalls of said holes provide walls of said wells which are substantially liquid impervious,
 a microporous material closing the bottom of each said hole,
 at least one three-dimensional spot of a crosslinked hydrogel polymer attached to only a portion of an upper surface area of said microporous material at the bottom of each of a plurality of said wells so that drainage can be effected through the portion of said surface area without said hydrogel polymer, and
 biological material so immobilized on or within the hydrogel polymer as to be contactable by liquid supplied to said well.

* * * * *